United States Patent [19]

Carlson

[11] 4,441,362

[45] Apr. 10, 1984

[54] METHOD FOR DETERMINING VOLUMETRIC FRACTIONS AND FLOW RATES OF INDIVIDUAL PHASES WITHIN A MULTI-PHASE FLOW REGIME

[75] Inventor: Norman R. Carlson, Houston, Tex.

[73] Assignee: Dresser Industries, Inc., Dallas, Tex.

[21] Appl. No.: 369,945

[22] Filed: Apr. 19, 1982

[51] Int. Cl.³ ............................................. E21B 47/00
[52] U.S. Cl. .................................... 73/155; 73/61.1 R
[58] Field of Search ........................... 73/155, 61.1 R; 324/351

[56] References Cited

U.S. PATENT DOCUMENTS

| | | | |
|---|---|---|---|
| 2,649,711 | 8/1953 | Dale | 73/155 |
| 3,258,963 | 7/1966 | Bryant et al. | 73/155 |
| 3,279,249 | 10/1966 | Tocanne | 73/153 |
| 3,437,924 | 4/1969 | Tocanne | 324/61 |
| 3,816,811 | 6/1974 | Cmelik | 324/61 R |
| 3,905,226 | 9/1975 | Nicolas | 73/155 |

OTHER PUBLICATIONS

Advertising Brochure, Resource Systems Company, Jul. 1981, p. 4.
Technical Paper, Pro-Data C. A.-The Hydro Logging Tool, by H. Cmelik, date uncertain.

*Primary Examiner*—Jerry W. Myracle

*Attorney, Agent, or Firm*—Richard M. Byron; Patrick H. McCollum

[57] ABSTRACT

A reference is established indicating the functional relation between differing proportions of one fluid phase within a mixture of a plurality of fluid phases to the dielectric response of that mixture. Measurements are taken within a well wherein the well fluid consists of multiple fluid phases, of the flow rate, density and dielectric response of the well fluid. The dielectric response measurement is related to the established reference to determine the apparent proportion or volumetric fraction of one fluid phase of the well fluid. The density measurement is utilized to determine the volumetric fraction of the same phase of the well fluid. These equivalent volumetric fraction determinations are utilized to adjust the established reference in response to the density-determined volumetric fractions such that subsequent dielectric response measurements within the well fluid may be correlated to such adjusted reference and thus may be translated into appropriate volumetric fraction values with improved accuracy. These volumetric fraction determinations may then be related to the flow rate measurement made within the well to obtain the flow rates of the individual phases of the well fluid at the depths at which the described measurements were made.

26 Claims, 14 Drawing Figures

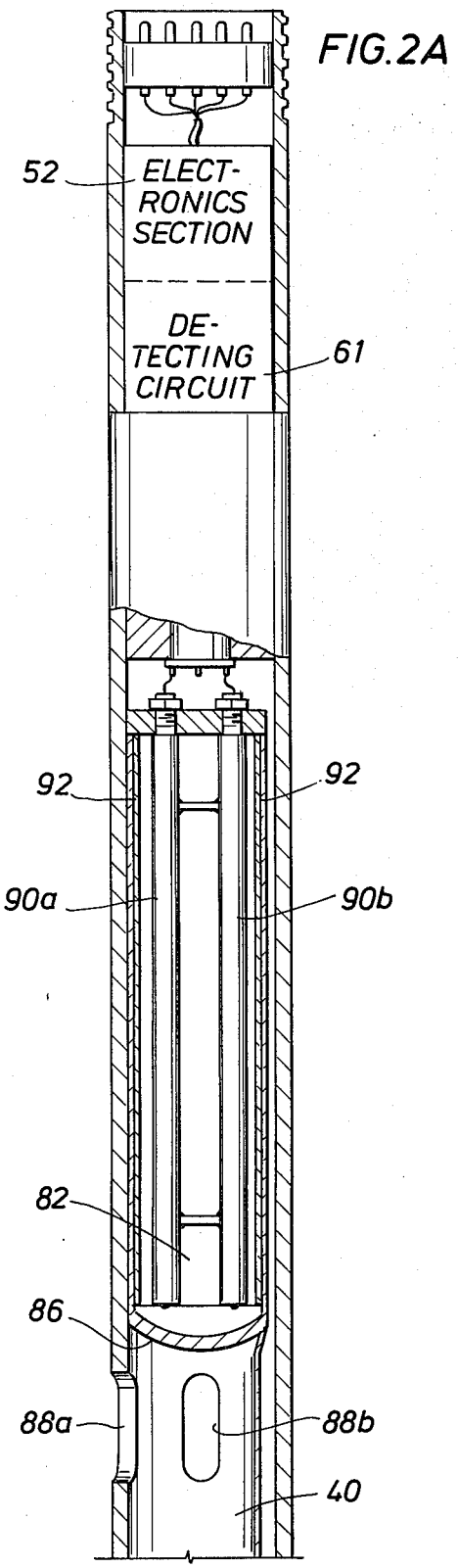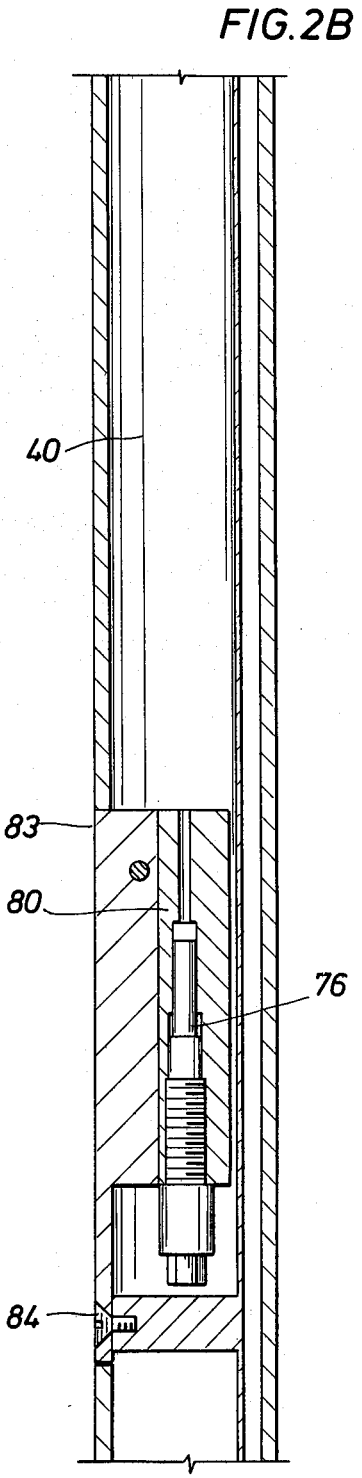

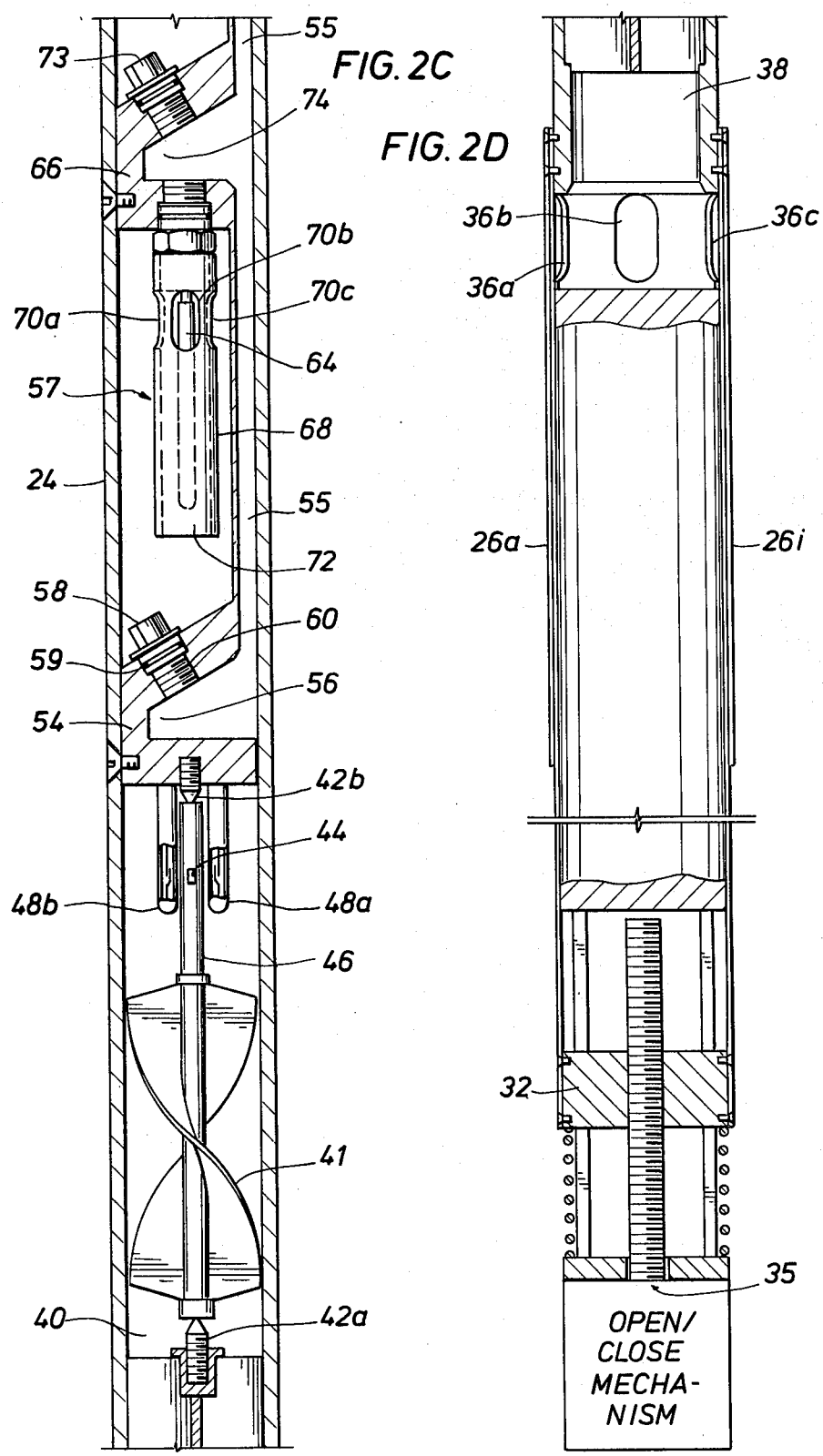

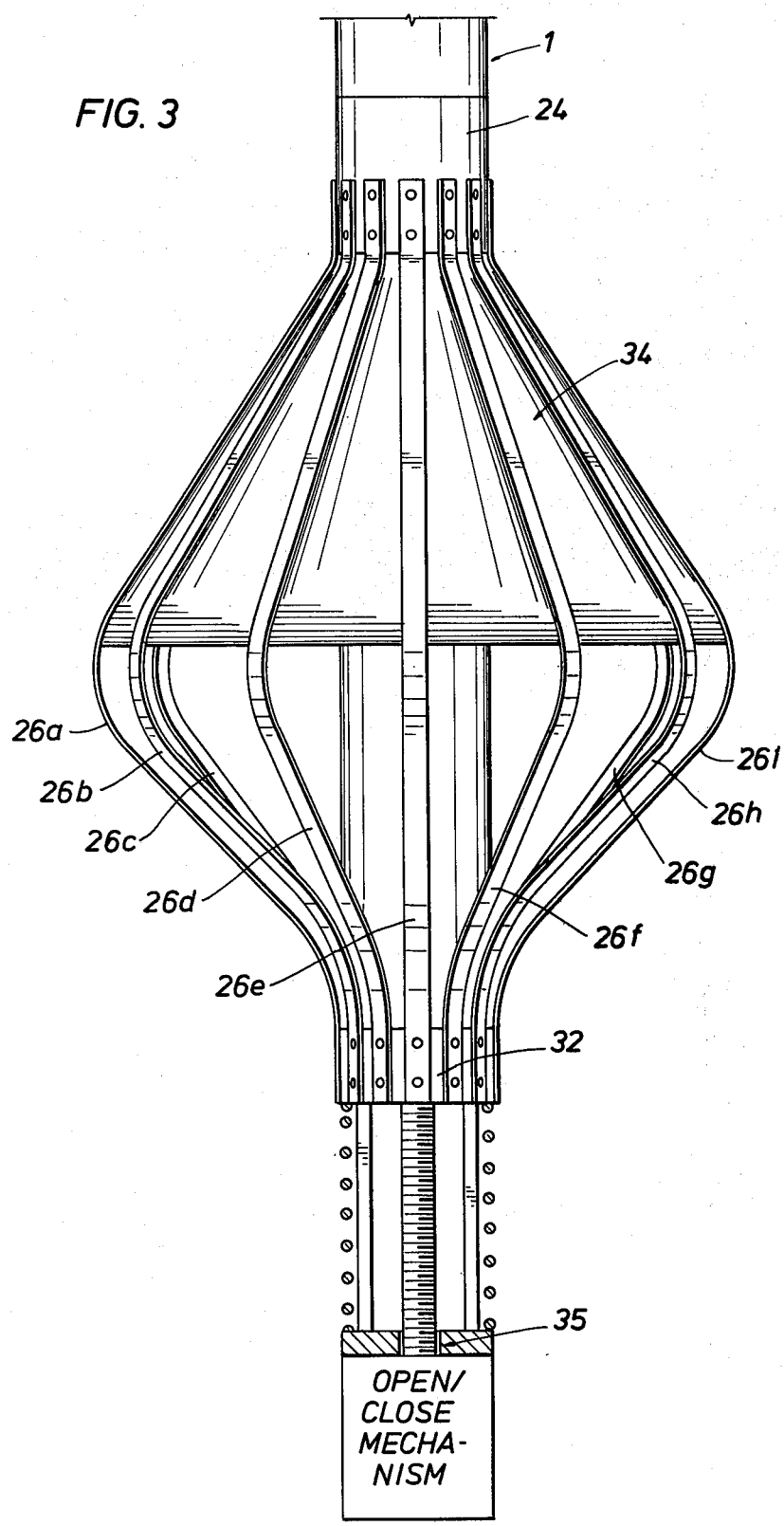

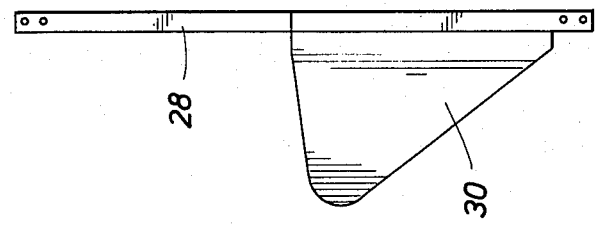
TO LINE DRIVER CIRCUITRY
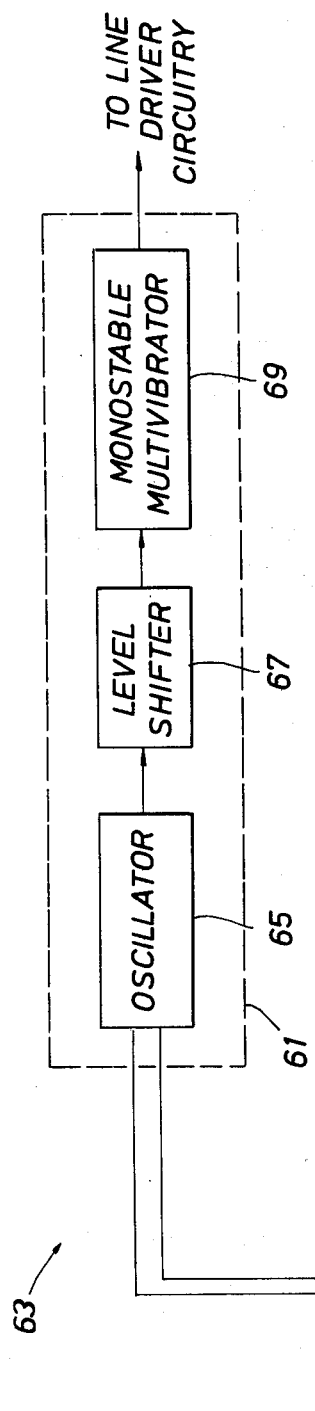
FIG. 4
FIG. 5
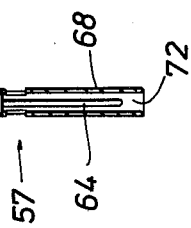

METHOD FOR DETERMINING VOLUMETRIC FRACTIONS AND FLOW RATES OF INDIVIDUAL PHASES WITHIN A MULTI-PHASE FLOW REGIME

BACKGROUND OF THE INVENTION

This invention relates generally to methods and apparatus for well logging, and more specifically relates to methods and apparatus for determining volumetric fractions and flow rates of individual phases in multi-phase flow regimes.

In producing wells it is no uncommon to find the well fluid flow regime consisting of multiple phases, such as oil and water, oil and gas, or oil, water and gas. Often, one or more of these phases is an undesired element in the well production flow. For example, in the case of a well fluid flow regime consisting of oil and water, the oil is typically the fluid phase desired to be produced and the water is typically an undesired phase in the production flow. When the degree of water present in the well production flow becomes excessive, logging surveys are run at a plurality of depth locations within the well to facilitate the determining of the flow rates of the individual phases at each of the locations. From these flow rate determinations, which will yield information regarding the depth locations and rates of water entry, remedial actions to control such water entry may be chosen.

Measurement of the flow rates of the individual fluid phases is complicated by the fact that not only do the individual phases of the flow regime flow at different velocities, referred to as phase slippage, but also the nature of the flow pattern of the phases is not uniform throughout cross-sections of the pipe. This non-uniformity of the flow pattern is caused by one or more of a multiplicity of phenomena which are known in the art, such as, for example, stagnation, heavy-phase fallback, and circulation, and is accentuated by such factors as large pipe, low flow rates, and/or deviated boreholes. Although the volumetric fractions of the individual fluid phases as determined across cross-sections of the well, also known as the phase holdups, are not uniform, they do bear a functional relationship to the flow rates of the individual phases across such cross-sections of the well, the exact nature of such functional relationship being dependent upon the conditions under which the fluid phase volumetric fractions were determined. Therefore, logging surveys to determine individual phase flow rates typically include measurements of the volumetric fractions represented by the individual phases.

So as to achieve a maximum of reliability of the volumetric fraction and flow rate determinations, it is desirable to determine the well flow characteristics while the well is actually producing. This is because an interruption of the well production may cause alterations in the flow characteristics of the well, including water entry, for which it is difficult or impossible to anticipate and/or compensate.

The oil and gas industry has attempted to determine the volumetric fractions of the individual fluid phases within these producing wells by conducting logging operations to determine either the density or the dielectric response of the well fluid. One means by which these determinations have been attempted has been by intersecting the fluid flow regime with the appropriate logging instrument while allowing the fluid flow to continue around the instrument. It can be appreciated, however, that this type of logging operation only determines the density or dielectric response of such portion of the fluid flow regime as actually engages the measuring system of the logging instrument. Therefore, fluid phases which do not intersect the instrument, or non-uniformities in the flow pattern caused by effects such as those described previously herein, which occur in the flow regime may cause the readings from the logging instrument to yield less than optimal data as to the nature of the fluid flow regime. Additionally, the accuracy of this type of surveying may be further complicated by the unknown effects upon the multi-phase flow regime when a logging tool is introduced into the producing well.

Further difficulties arise in determining the correct volumetric fractions of the fluid phases once the density or dielectric response measurement is obtained. Because the average density of the well fluid is generally the volumetrically proportional average of the densities of the individual phase components of the fluid flow regime, the density of the well fluid varies in a generally linear functional relation to changes in the volumetric fractions of the individual phases in the fluid flow regime. The fluid density measurement, however, typically offers a less than optimal degree of resolution of the individual phase volumetric fractions when the well fluid is composed of certain fluids, for example, water and oil, partially because of the relatively similar densities of the fluids, approximately 1 for water and 0.8 for oil, at surface conditions. In contrast to this, a fluid capacitance instrument which measures the dielectric response of the fluid, such dielectric response being directly related to the dielectric constant of the fluid, offers a measurement of a relatively high degree of resolution of the phase volumetric fractions present in the measured fluid due to the relatively disparate dielectric constants of water, approximately 78 at surface conditions, and of oil and gas, approximately 3 and 1, respectively, at surface conditions. This simple dielectric response measurement is difficult, however, to correlate to accurate phase volumetric fractions because the conductivity and dielectric properties of some fluids, including oil and water, are known to vary substantially with temperature. Further, the presence of other fluids or dissolved solids within the well fluid may alter the dielectric response of the well fluid. Therefore, calibrations of the fluid capacitance instrument dependent solely upon characteristics observed under surface conditions may lack validity when related to measurements taken within the borehole environment. Additionally, the dielectric properties of a mixture of oil and water or gas and water have been determined to be not always a linear reflection of the volumetrically proportional average of the relative dielectric response characteristics of the two fluids.

Accordingly, the present invention overcomes the deficiencies of the prior art by providing a method and apparatus by which a fluid dielectric response measurement may be interpreted in view of survey conditions, thereby facilitating a functional determination of the volumetric fractions and flow rates of individual fluid phase components within a multi-phase flow regime.

SUMMARY OF THE INVENTION

The dielectric response of a fluid flow regime is determined, such as by mixing the fluid flow regime into a generally uniform or homogenous mixture and by intersecting such mixture with a dielectric response sensor suitable for generating a signal indicative of dielectric response characteristics of the mixture. The density of the fluid flow regime is measured, such as again by mixing the fluid flow regime into a generally uniform mixture and by measuring the penetration of gamma radiation through the mixture.

A reference is established for the dielectric response sensor indicating the functional relationships between sensor response values within a fluid mixture of at least two phases and the volumetric fraction of at least one of the phases in the fluid mixture. In a preferred embodiment, the fluid phases within this fluid mixture are essentially equivalent to the fluid phases within the fluid flow regime of the well. The apparent volumetric fraction of at least one of the phases within the well fluid flow regime is determined by interpreting the dielectric response signal obtained within the fluid flow regime in accordance with the established reference. The volumetric fraction of the same phase of the fluid flow regime is also determined in response to the measured density of the fluid flow regime.

The established dielectric response reference is adjusted in response to the density-derived volumetric fraction determination. In a preferred embodiment, the density and dielectric response measurements, and accompanying volumetric fraction determinations of the one phase, are made at each of two different depth locations within the fluid flow regime. The difference in the dielectric response-inferred volumetric fraction determinations is determined and the dielectric response reference is divided into a plurality of intervals over the range at least between the dielectric response-inferred volumetric fraction values. A participation factor of each interval is determined by relating the change in the volumetric fraction as indicated by the reference over each interval to the total change in the dielectric response-inferred volumetric fractions of the one fluid phase. The participation factors are related to the change in the volumetric fraction as determined from the two density measurements. Over a range of intervals similarly representing changes in dielectric response, the participation factor of each interval is compared to the total change in the density-determined volumetric fraction to obtain an adjusted change in volumetric fraction over each interval. The functional relationship between dielectric response signal values and volumetric fractions are then sequentially linearly approximated across each interval to obtain an adjusted reference. Subsequent dielectric response measurements of the fluid flow regime may be translated into volumetric fractions of the one phase in response to this adjusted reference.

Measurements of the total flow rate of the fluid flow regime may also be made by appropriate apparatus. The flow rate of at least one phase of the fluid flow regime may then be determined in relation to such total flow rate measurement and to the described volumetric fraction determinations.

Accordingly, the present invention provides a method and apparatus whereby dielectric response measurements of a fluid flow regime may be interpreted in view of actual environmental conditions to determine volumetric fractions of individual phases within such fluid flow regime with improved accuracy and whereby flow rates of the individual phases may similarly be obtained in reference to such volumetric fractions with heightened accuracy.

BRIEF DESCRIPTION OF THE DRAWINGS

FIGS. 2 A-D illustrates, in a side view and partially in cross-section, a logging instrument in accordance with the present invention.

FIG. 3 illustrates that portion of the logging instrument of FIG. 2D, shown in operating configuration and partially in cross-section.

FIG. 4 illustrates a single deflector spring of that portion of the logging instrument of FIG. 2D and FIG. 3.

FIG. 5 illustrates in block diagram form the dielectric response sensor of the instrument of FIG. 2.

DETAILED DESCRIPTION OF THE PREFERRED EMBODIMENT

Figure 1:
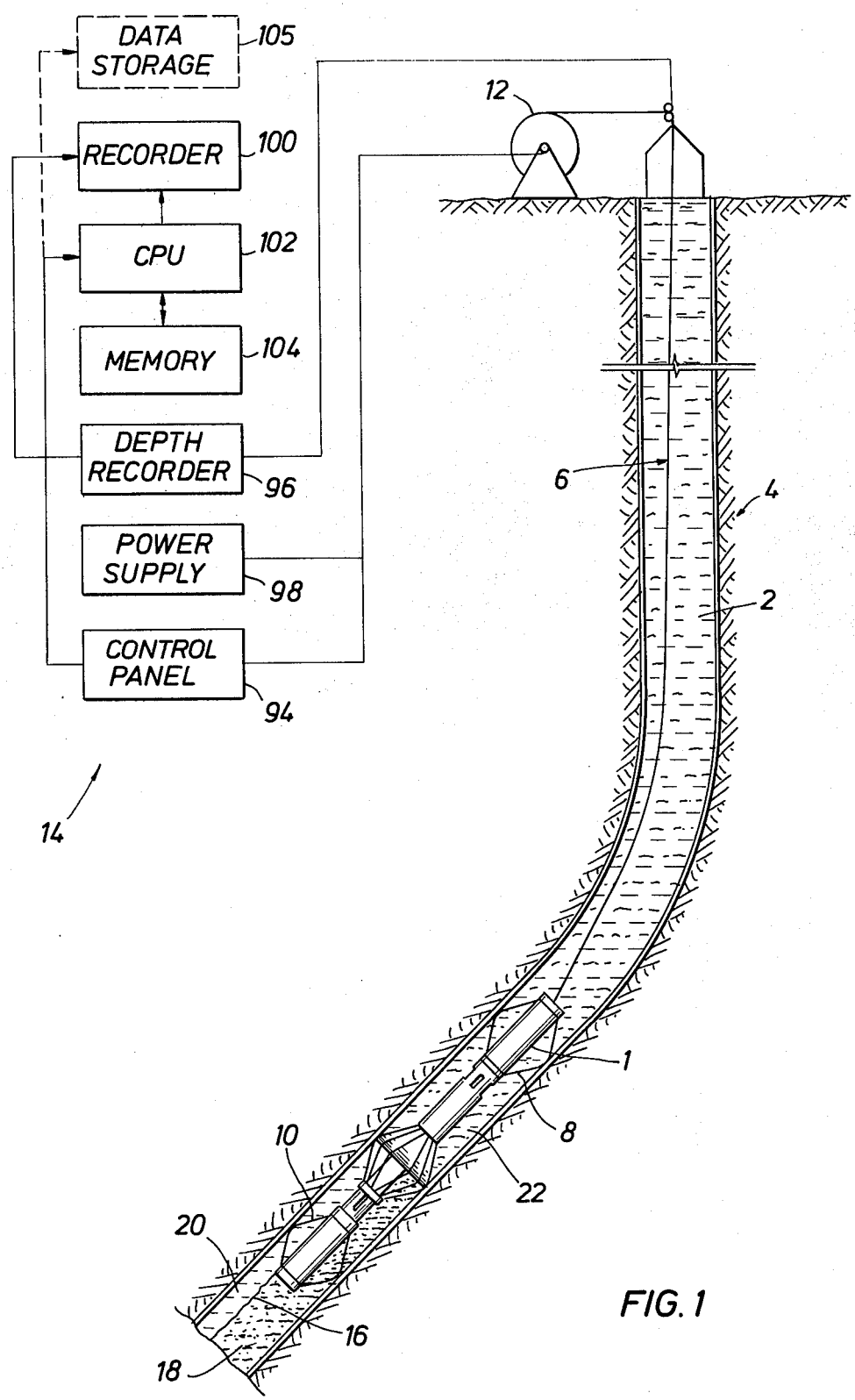
FIG. 1 illustrates a logging instrument in accordance with the present invention, disposed within a well, shown partially in cross-section, in operating configuration.

Referring now to the drawings in more detail, particularly to FIG. 1, therein is illustrated a deviated cased borehole or well 2, penetrating an earth formation 4, shown in vertical cross-section. It is to be understood that although the illustration shows a well in which casing has been set, the present invention may also be employed in an uncased well. Disposed within well 2, and suspended from cable 6, is a density/capacitance/flowmeter logging instrument 1 for determining volumetric fractions and flow rates in multi-phase flow regimes in accordance with the present invention. Instrument 1 is positioned proximate the longitudinal axis of well 2 by centralizers 8 and 10. Shown in well 2, below instrument 1, is a two-phase fluid flow, illustrated generally at 16. A two-phase fluid flow is not uncommon in producing wells. For purposes of illustration, this two-phase flow will be discussed as consisting of water and oil, a combination which is also not uncommon in such producing wells. Where the two-phase fluid flow 16 consists of water and oil, water 18 will flow generally toward the lower side of the well bore while oil 20 will flow above water 18 due to its lesser density. Above instrument 1 in well 2, this previously two-phase fluid flow is shown as a generally uniform mixture 22 due to the operation of instrument 1 as will be described later herein.

At the earth's surface there is illustrated a hoist 12 and surface electronics, generally illustrated at 14, in a configuration well known in the well logging art. Surface electronics 14 includes a control panel 94 which contains conventional electrical switching and adjustment apparatus for controlling logging instrument 1 within well 2, a depth recorder 96 which generates an electrical signal indicative of the degree of longitudinal movement of logging instrument 1 within well 2, and a power supply 98 which supplies the electrical power necessary to operate logging instrument 1. Control panel 94 is adapted to process the electrical signals received from logging instrument 1 and to yield signals suitable for communication to Central Processing Unit (CPU) 102. A suitable memory unit 104 and recorder 100 are also cooperatively coupled to CPU 102. It will be appreciated that if complete or partial processing of the signals is desired to occur at a remote time or location it will be preferable to include a suitable form of data storage 105 in surface electronics 14, such as a magnetic tape storage, which is suitably interfaced with control panel 94 and/or CPU 102.

Referring now to FIGS. 2 A-D of the drawings, therein is shown density/capacitance/flowmeter logging instrument 1 in greater detail and partially in cross-section. Instrument 1 includes and is constructed upon an elongated body member 24 which is adapted to traverse an earth borehole.

Referring now to FIG. 3, therein is illustrated that portion of density/capacitance/flowmeter instrument 1 of FIG. 2D, shown in operating configuration and partially in cross-section. In the preferred embodiment, a plurality of deflector springs 26a, 26b, 26c, 26d, 26e, 26f, 26g, 26h and 26i are disposed essentially equidistantly around the periphery of body member 24. Each deflector spring 26a, 26b, 26c, 26d, 26e, 26f, 26g, 26h or 26i is composed of an elongated bow spring (28 in FIG. 4), with a deflector fin (30 in FIG. 4) firmly affixed thereto by spot welding or other suitable means. Deflector springs 26a, 26b, 26c, 26d, 26e, 26f, 26g, 26h and 26i are interlayed with one another, the laterally extending portion of the spring fitting closer to body member 24 than the spring immediately to its side. The preferred embodiment would have approximately 10-14 of these deflector springs, and most preferably would have 12 deflector springs. Each spring 26a, 26b, 26c, 26d, 26e, 26f, 26g, 26h and 26i has a first end fixedly mounted toward the proximal end of instrument 1 and a second end mounted to collar 32 which is slidably mounted on body member 24. Coupled to collar 32 is an open/close mechanism 35, preferably a motor-driven, screw-type mechanism of a type known in the art. Open/close mechanism 35 is actuated by means of a first command signal from surface electronics 14, and is designed to move collar 32 toward the proximal end of instrument 1, (as illustrated in FIG. 3), and, upon a second command signal from surface electronics 14, to withdraw collar 32 back toward the distal end of instrument 1 (as illustrated in FIG. 2D).

When collar 32 is located toward the proximal end of instrument 1, deflector springs 26a, 26b, 26c, 26d, 26e, 26f, 26g, 26h, and 26i are forced out and away from body member 24. This causes deflector springs 26a, 26b, 26c, 26d, 26e, 26f, 26g, 26h and 26i, acting together, to form a generally tapered collector 34, most preferably a funnel configuration, virtually blocking the passage of fluid around instrument 1 within well 2 (as illustrated in FIG. 1). The function of tapered collector 34 will be described more fully later herein in the discussion of the operation of instrument 1.

Referring again to FIG. 2, particularly to FIGS. 2C-D, inside the bore and proximate the apex of the aforementioned tapered collector (illustrated at 34 in FIG. 3), are located a plurality of entrance apertures 36a, 36b, 36c preferably spaced essentially equidistantly around the periphery of body member 24. Entrance apertures 36a, 36b, 36c connect with passage 38, further connecting to a chamber 40 in body member 24, facilitating fluid communication between collector 34 and chamber 40.

Chamber 40 contains a rotor 41 freely rotatably mounted on a longitudinal axis between two opposing pivots 42a and 42b and conformed so as to be rotationally responsive to the flow of fluid through chamber 40. Associated with rotor 41 is a measuring device for detecting the rotational speed of rotor 41. In the preferred embodiment this measuring device is a combination of a magnet 44 mounted on rotor trunnion 46 and a plurality of magnetic reed switches 48a, 48b disposed in proximity to and around trunnion 46. Reed switches 48a, 48b are connected to a suitable power source within electronics section 52, preferably a 25 volt d.c. power source, so that as magnet 44 rotates past each switch 48a or 48b, that switch alternately opens and closes, thereby generating an electrical pulse representative of one rotation of trunnion 46 past that individual switch 48a or 48b. The pulses from switches 48a and 48b are then coupled to electronics section 52 to generate a first electrical signal representative of the rotational speed of rotor 41. Electronics section 52 amplifies this first electrical signal by means of conventional line driver circuitry to prepare the signal for transmission through electrical conductors in cable 6 to surface electronics 14. It will be appreciated that reed switches 48a and 48b and one pivot 42b supporting rotor trunnion 46 are mounted on first support 54 which is suitably formed to provide a minimum of impedance to the flow of fluid through chamber 40. First support 54 contains a chamber 56, connecting with passage 55, such passage 55 for containing electrical signal carrying wires (not illustrated) connecting reed switches 48a and 48b to electronics section 52. Access to the wires is provided by means of aperture 60 in support 54. Aperture 60 is suitably sealed by plug 58 so as to isolate chamber 56 from the well fluid when instrument 1 is within well 2. Plug 58 is preferably threadably coupled to aperture 60 with a fluid-tight seal being provided by o-ring 59 which is installed on plug 58 in a conventional manner.

Also located within chamber 40 is probe 57 of the dielectric response sensor. In the preferred embodiment, probe 57 includes an elongated rod electrode 64, preferably of from three to seven inches in length, suitably mounted to a second support 66 and preferably extending generally longitudinally within chamber 40. In the preferred embodiment of the invention, probe 57 also includes a hollow cylindrical elongate electrode 68 which extends coaxially with rod electrode 64, although it is to be understood that body member 24 may be adapted to serve as this second electrode or that an independent electrode of a different conformity may be utilized. Located near the base of cylindrical electrode 68 are a plurality of apertures 70a, 70b, and 70c suitably formed to allow passage of fluid from within annulus 72 between electrodes 64 and 68, to the general confines of chamber 40. At least one of electrodes 64 or 68, preferably central rod electrode 64, is electrically isolated from both body member 24 and the other electrode. It will be appreciated that at least one and preferably both electrodes 64 and 68 are additionally electrically isolated from a fluid flowing within chamber 40. This is accomplished by coating electrodes 64 and 68 with an electrically insulatint coating suitable for withstanding the temperatures and pressures of the well environment.

Referring now to FIG. 5, therein is illustrated dielectric response sensor 63 of instrument 1. Electrodes 64 and 68 of probe 57 act as the plates of a capacitor, the capacitance of whicn is determined by the dielectric response of the medium occupying annulus 72. Many forms of circuitry are suitable for generating an electrical signal indicative of this dielectric response. In the preferred embodiment of the invention, dielectric response sensor 63 includes a detecting circuit 61, preferably located within the electronics section (52 in FIG. 2). Detecting circuit 61 is designed to generate a frequency modulated signal representative of the dielectric response of the medium within annulus 72 of probe 57. Detecting circuit 61 preferably includes a high frequency pulse oscillator 65, the frequency of which is determined by a resistance-capacitance network, of which the resistance is fixed at a predetermined value and the capacitance is established through the medium within annulus 72. The output of oscillator 65 is coupled to suitable electronic circuitry, such as a level shifter 67 and a monostable multivibrator 69 for establishing a uniform pulse height and width in the dielectric response signal. This second electrical signal is then amplified by conventional line driver circuitry to prepare the signal for transmission to surface electronics 14. Dependent upon the frequency range of oscillator 65, it may be desirable to insert suitable divider circuitry (not illustrated), preferably between level shifter 67 and monostable multivibrator 69 to proportionately reduce the number of pulses contained within the signal, thereby optimizing the signal for communication to surface electronics 14.

Referring again to FIG. 2C, second support 66 is adapted similarly to first support 54 to allow the free passage of fluid through chamber 40 and similarly contains a chamber 74 connecting with passage 55 for housing electrical signal-carrying wires (not illustrated) connecting electrode 64 and 68 to detecting circuit 61 located within electronics section 52. Access to chamber 74 is again provided by a plug 73 in a manner similar to that described previously herein with respect to first support 54.

Referring now to FIGS. 2 A-B, also located within chamber 40 is a means for determining the density of the well fluid. The preferred embodiment utilizes radioactive means, preferably gamma radiation, for making this density determination. Gamma rays are electromagnetic radiations which have the capability of penetration through matter. As gamma radiation passes through a sample of matter, some of the radiation will fail to fully penetrate the sample, predominately due to the effects of three interactions; photo-electric absorption, compton scattering, and pair production, all of which occur in degrees relative to the density of the irradiated matter. Therefore, penetration bears an inverse relationship to the density of the matter, such that the greater the density of the substance, the smaller the penetration. It is possible to measure this decrease in penetration and therefore the density of a sample of matter by causing a beam of gamma rays from a radiation source to pass through the sample and strike a detector. By correlating the measured gamma ray penetration through that matter with calibration measurements of gamma ray penetration for the source and detector through substances of known densitites the density of the sample may be determined.

In this preferred embodiment, a nuclear source 76, which is preferably a chemical gamma ray source, and most preferably is a chemical cesium-137 source emitting gamma rays with an energy of approximately 0.661 Mev., is situated within body member 24 and is mounted within a block 80 which collimates the gamma radiation emitted by source 76 into a beam which longitudinally traverses a portion of chamber 40 to impinge detector 82. It will be appeciated that block 80, to perform the desired collimation, is constructed of a suitably dense material, preferably tungsten. Block 80 is attached to access plate 83 which is preferably pivotally attached to body member 24 to facilitate access to source 76. While logging, plate 83 is secured in a closed position (as illustrated in FIG. 2B) by conventional means, such as a screw 84. Plate 83 and block 80 are suitably formed such that when plate 83 is in the closed position, plate 83 and block 80 both define a portion of the perimeter of chamber 40 and allow the flow of fluid through chamber 40 with a minimum of impedence to the flow.

Located in body member 24 between source 76 and detector 82 is a relatively unobstructed portion of chamber 40. Detector 82 lies proximate the end of this portion of chamber 40, the limit of such chamber 40 being defined by pressure dome 86 covering the end of detector 82, such dome 86 being constructed of a suitable material, preferably steel, and of a suitable thickness so as to withstand the pressure in the well and protect detector 82 from the fluid environment of chamber 40 while still allowing penetration to detector 82 by the gamma radiation. Located proximate the end of chamber 40 which is defined by dome 86 are a plurality of apertures 88a and 88b to allow the passage of fluid from chamber 40 into well 2 after traversal of at least the majority of that portion of chamber 40 which is located between source 76 and detector 82.

Detector 82 consists of an apparatus for detecting the radiation emitted by source 76, preferably one or more geiger counter tubes or, alternatively, a scintillation crystal and photomultiplier tube, most preferably consisting of eight geiger tubes 90a, 90b, (for clarity, only two geiger tubes are illustrated here) which emit electrical impulses when impinged by gamma rays from source 76. Detector 82 is surrounded on the sides by suitable shielding material 92, preferably tungsten shielding, to minimize the impinging of detector 82 by radiation other than that emitted by source 76, such as radiation occurring naturally in the earth formations surrounding well 2. The outputs of all geiger tubes 90a and 90b are connected in parallel to sum the outputs thereof into a single detector signal. This detector signal is coupled to electronics section 52 which amplifies this third electrical signal, again by conventional line driver circuitry, to prepare the signal for transmission to surface electronics 14.

Referring now to FIGS. 1, 2 and 3 generally, in the normal operation of density/capacitance/flowmeter instrument 1, instrument 1 is lowered in well 2 to the depth at which a measurement is desired. Surface electronics control panel 94 is utilized to generate a first command signal actuating open/close mechanism 35 in instrument 1, causing collar 32 to be moved toward the proximal or uphole end of body member 24, thereby causing deflector springs 26a, 26b, 26c, 26d, 26e, 26f, 26g, 26h and 26i to form a tapered collector 34 as described earlier herein. As collector 34 is formed and expanded, preferably to the approximate diameter of well 2, collector 34 virtually blocks the flow of fluid around instrument 1, channeling the fluid toward apertures 36a, 36b, 36c and passage 38 in body member 24 which form the throat of collector 34. It is to be appreciated that as the inner diameter of collector 34 narrows, due to the constant flow rate of the well fluid, the linear velocity of the fluid flowing through collector 34 increases significantly. As the accelerating fluid phases converge toward the throat of collector 34, apertures 36a, 36b, and 36c divide the flow and a turbulence is created which causes the individual phases of the fluid flow regime to blend together into a single mixture of generally uniform composition. Additionally, the gradual channeling accelerates the fluid flow without excessively disturbing the relative flows of the fluid phases as they exist below instrument 1. This nondisturbance allows the creation of a generally homogeneous mixture of the phases without significantly disturbing the relative composition of the mixture as compared with the relative composition of the fluid flow regime as it exists below instrument 1.

This mixture then travels through passage 38 to chamber 40. The mixture contacts and passes rotor 41 causing it to rotate, the exact rotational speed being dependent upon and indicative of the total flow rate of the fluid in well 2. The rotational speed of rotor 41 is detected and converted into a plurality of pulsed electrical signals which are then summed and amplified by electronics section 52 into a first electrical signal which is then transmitted over cable 6 to surface electronics 14 as described earlier herein. Simultaneously with providing an indication of the fluid flow rate, the rotation of rotor 41 serves to further enhance the blending of the multiple fluid phases into one generally uniform mixture.

The mixture travels through chamber 40 to the location of dielectric response sensor electrodes 64 and 68. A portion of the generally uniform mixture will enter annulus 72 in probe 57, changing the capacitance in sensor detecting circuit 61, thereby yielding a second electrical signal functionally related to the dielectric response characteristics of the mixture as discussed earlier herein. This sensor signal is amplified and transmitted to surface electronics 14 as described earlier herein. It will be appreciated that apertures 70a, 70b and 70c at the base of cylindrical electrode 68 allow the mixture to flow freely longitudinally through annulus 72 between electrodes 64 and 68.

The mixture continues to traverse chamber 40 to reach that portion housing the density-determining apparatus described earlier herein. The beam of radiation from source 76 traverses at least a portion of the mixture and impinges detector 82, yielding a third electrical signal functionally representative of the relative density of the mixture. This third electrical signal is similarly communicated to surface electronics 14.

Control panel 94 of surface electronics 14 receives the three electrical signals communicated to the surface over cable 6 and adapts the signals for communication of CPU 102. It will be appreciated that when the signals are transmitted to control panel 94 as a series of pulses, as is a convenient means for the embodiments of the detector devices described herein, control panel 94 will preferably include counters (not illustrated), having a digitized output of a suitable resolution, which communicate the digitized data to CPU 102 at an established repetition rate. Alternatively, the data may be digitized downhole, within electronics section 52 of instrument 1, and control panel 94 may merely buffer such data for transmission to CPU 102. CPU 102 processes the data represented by the three signals in the manner to be described later herein and signals representative of the processed data are communicated to recorder 100 for graphic representation thereby.

As stated earlier herein, the dielectric constant of a mixture of two fluids having dissimilar dielectric constants, while offering a high degree of resolution of the volumetric fractions of the constituent phases of the mixture, is generally not a linear, volumetrically proportional combination of the measured dissimilar dielectric constants of the individual fluids. Also as stated earlier herein, the dielectric constants of the two fluids may change significantly under the temperatures and pressures of the borehole environment.

Figure 6:
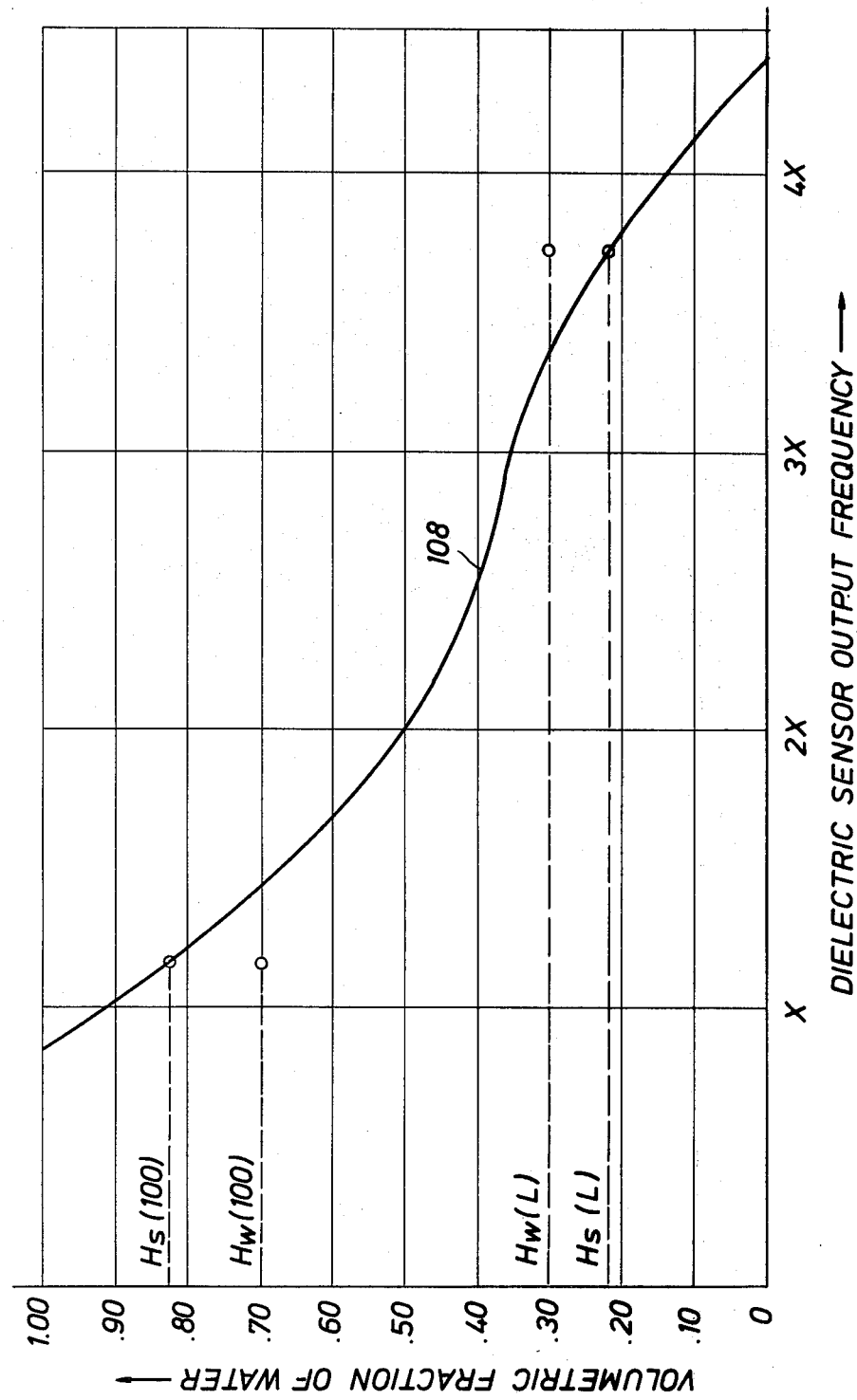
FIG. 6 illustrates graphically the functional relationships between the output frequency of one embodiment of a dielectric response sensor within an oil-water mixture to the volumetric fraction of water within that mixture.

Referring now to FIG. 6, therein is graphically illustrated a reference of the functional relationships of the dielectric response of a mixture of oil and water to the relative volumetric fraction of water within the mixture, as such dielectric response and functional relationships are determined by one embodiment of a dielectric response sensor under surface conditions, thereby reflecting a response curve 108 for that dielectric response sensor in an oil-water mixture at surface conditions. It will be appreciated that response curve 108 and the functional relationships illustrated therein are for example only and that alternative embodiments of dielectric response sensors or curves established under differing conditions or for mixtures of different fluids, may exhibit differing functional relationships which may be utilized in accordance with the present invention. By interpreting a dielectric response measurement made within a well with regard to such functional relationships as those expressed by such response curve 108, and translating such functional relationships in view of known downhole conditions, the volumetric fractions of the individual downhole fluid phases may be determined with a heightened degree of accuracy. From these volumetric fractions and the measured total flow rate of the well fluid at a corresponding depth, the flow rates of each fluid phase may then be determined.

In the preferred practice of the present invention, the functional relationships expressed in response curve 108 are translated in response to density and dielectric response measurements made within the portions of the fluid flow regime exhibiting the maximum and minimum volumetric fractions of water. One means of determining the depth locations within the well at which the maximum and minimum volumetric fractions of water are located is to survey the well, operating density/capacitance/flowmeter instrument 1 within the well, preferably at locations above each horizon of perforations through which fluid is entering the well. By monitoring the signal from the density sensor of instrument 1 for values indicative of maximum and minimum densities, the depth locations exhibiting the maximum and minimum volumetric fractions of water may be determined. Instrument 1 will then be returned to these two depth locations where measurements will be taken with all three sensors of instrument 1.

Figure 7:
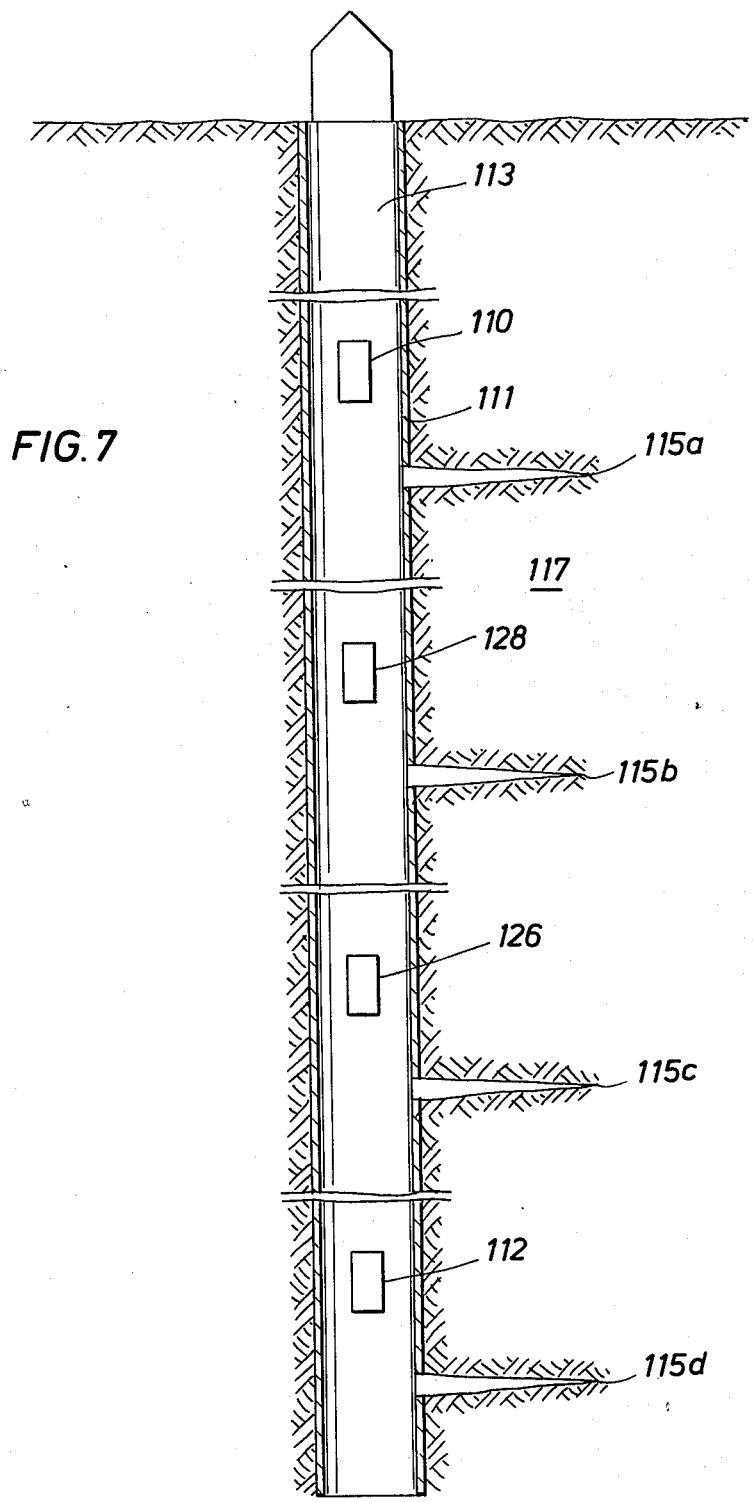
FIG. 7 illustrates a well, shown in vertical section, containing a plurality of depth measurement locations situated relative to perforations in the well casing and adjacent earth formations.

Referring now to FIG. 7, therein is illustrated a well 113 containing a plurality of depth measurement locations 110, 112, 126, and 128 situated relative to perforations 115a, 115b, 115c and 115d in well casing 111 and earth formation 117. In the practice of the present invention, logging instrument 1 is lowered to the depth location within well 113 at which the maximum volumetric fraction of water within the fluid flow regime was located (shown at 110 for purposes of illustration). Measurements of the flow rate, dielectric response and density of the well fluid flow regime are taken in the manner described earlier herein. It will be understood that to minimize statistical error, the measurements represented by the three described signals are taken for a pre-determined increment of time, preferably approximately one to two minutes, dependent upon the statistical response of the sensing devices. For the electrical signal of each sensing device, CPU (102 in FIG. 1) will preferably determine the simple average of the total signal values represented to yield a statistically accurate single value measurement. Instrument 1 is then lowered in well 113 to the depth location at which the minimum volumetric fraction of water was located (shown at 112 for purposes of illustration). Measurements are again taken of the flow rate, dielectric response and density of the well fluid for a similar time interval, and each of the sensor electrical signals is again averaged to yield single values for each of the measurements. It is to be understood that these measurements may be made at depth locations 110 and 112 in reverse order from that described herein.

As discussed earlier herein, the fluid density measurement of the mixture of the fluid flow regime allows a generally accurate and linear, if relatively low resolution, functional indication of the volumetric fractions of the phases present in the fluid flow regime. The functional relation of the measured mixture density at each depth measurement location to the volumetric fraction of water at that location is expressed by the relation:

$$H_w = \frac{\rho_m - \rho_o}{\rho_w - \rho_o} \tag{1}$$

where $H_w$ represents the volumetric fraction of water, $\rho_m$ represents the measured mixture density, and $\rho_o$ and $\rho_w$ represent the density of the oil and water, respectively. The terms $\rho_o$ and $\rho_w$ may be determined by fluid samples taken at the surface of the well, however, in equation 1 all densities must be at equivalent conditions of temperature and pressure, therefore, either $\rho_o$ and $\rho_w$ must be correlated to downhole survey conditions or $\rho_m$ must be converted to an equivalent value under surface conditions, either adjustment being accomplished using correlations known to the well logging industry. Because in an oil-water flow such as that used for example, the remainder of the flow volume will consist of the oil phase, the volumetric fraction of oil ($H_o$) may be determined by the relation:

$$H_o = 1 - H_w \tag{2}$$

The volumetric fraction of water should be determined from the mixture density measurements taken at each depth location 110 and 112, bearing cognizance that the values of $\rho_w$ and $\rho_o$ may change depending upon the significance of any difference in the borehole conditions at the depths of the individual measurements.

The dielectric response values determined by CPU (102 in FIG. 1) may now be compared to the functional relationships between such response values and the volumetric fractions of water as determined at surface conditions, relfected by response curve 108 in FIG. 6. The apparent volumetric fractions of water as measured by the dielectric response sensor may thus be determined for the maximum or 100% volumetric fraction measurement location 110 and the minimum or lowest volumetric fraction measurement location 112.

It will be appreciated that the volumetric fractions of water determined in accordance with the measured mixture density at each measurement location, represented as $H_w(100)$ for the maximum or 100% volumetric fraction and $H_w(L)$ for the minimum or lowest volumetric fraction, are determinative of the same parameters as are the volumetric fractions of water inferred from surface response curve 108 of the dielectric response sensor, represented as $H_s(100)$ and $H_s(L)$ for maximum and minimum volumetric fractions, respectively, discrepancy being induced into the volumetric fractions inferred from the dielectric response sensor due to the effects of the downhole conditions upon the dielectric properties of the fluid as discussed earlier herein. The four aforementioned volumetric fraction values are plotted in FIG. 6 relative to response curve 108, from which the dielectric response-inferred volumetric fractions, $H_s(100)$ and $H_s(L)$ were determined. The density-determined volumetric fractions $H_w(100)$ and $H_w(L)$ are illustrated in appropriate ordinate alignment with the dielectric response value coordinates on response curve 108 because they are representative of equivalent parameters. The density-determined parameters are illustrated in FIG. 6 as widely disparate from the correllative dielectric response-determined parameters for purposes of clarity of illustration. Because both sensor measurements are of equivalent parameters, it is possible to normalize the response characteristics of the dielectric response sensor represented by response curve 108, with reference to the density-determined volumetric fractions of water, $H_w(100)$ and $H_w(L)$ for maximum and minimum volumetric fraction measurements, respectively.

The apparent volumetric fractions of water at maximum and minimum flow as measured by the dielectric response sensor, $H_s(100)$ and $H_s(L)$, respectively, are utilized to determine the apparent total change in the volumetric fraction of water ($\Delta H_s$), as represented by the relation:

$$\Delta H_s = H_s(100) - H_s(L) \tag{3}$$

Figure 8:
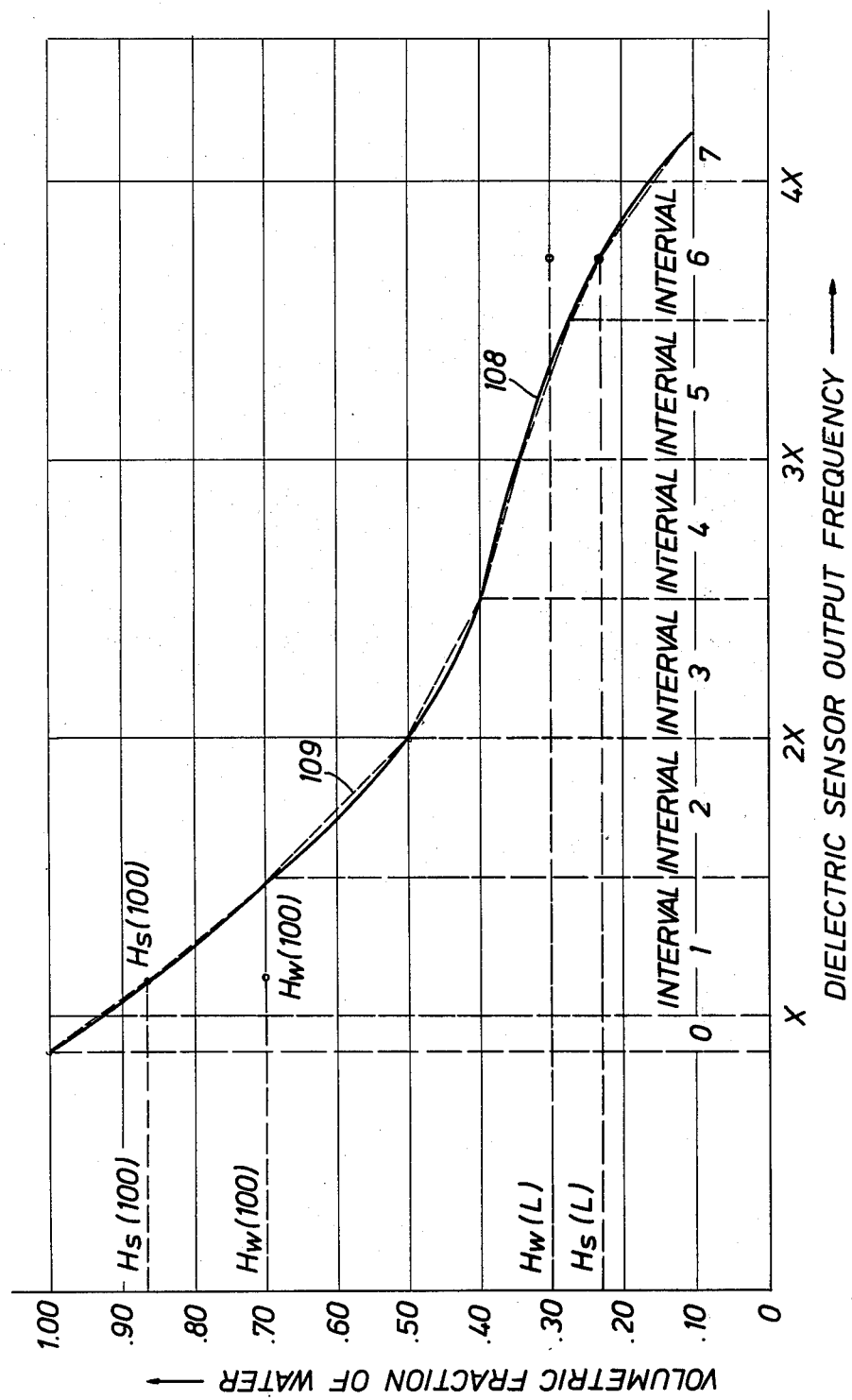
FIG. 8 illustrates graphically the dielectric sensor response curve of FIG. 6, divided into a plurality of intervals and a linear approximation of such curve across each interval.

Referring now to FIG. 8, the output signal frequency range of the dielectric response sensor is divided into a plurality of intervals, at least over the range of the apparent total change in the volumetric fraction of water ($\Delta H_s$) and preferably spanning the entire output frequency range of the sensor. Each interval represents a span of change in the output frequency of the dielectric response sensor, for example, each interval may span a 250 Hz change in the output frequency of the sensor. The number of these intervals is variable, depending upon the degree of resolution desired in the normalization. In the preferred practice of the invention, six equal length intervals are utilized, accompanied by two odd length intervals added at each extreme of the six equal length intervals so as to span the complete frequency range of the dielectric response sensor. It will be appreciated that any output signal value of the dielectric response sensor corresponds to a volumetric fraction of water, the value of such volumetric fraction determined by a functional relationship, as expressed in response curve 108 (solid curve of FIG. 8). Therefore, as this output signal range is divided into a plurality of intervals the corresponding functional relationships are also divided into a plurality of intervals. This is depicted graphically in FIG. 8. Over the range of each interval the corresponding functional relationships described above may be considered as being generally linear, therefore response curve 108 may be closely approximated by a series of straight lines 109 (dashed lines of FIG. 8) across the span of each interval.

In a case such as illustrated in FIG. 8, wherein $H_s(100)$ intersects response curve 108 in interval 1 and $H_s(L)$ intersects curve 108 in interval 6, the total change in the apparent volumetric fraction of water ($\Delta H_s$) is the sum of the changes in the apparent volumetric fraction of water across each of these intervals. Therefore, representing the number of each interval in parentheses:

$$\Delta H = \Delta H_s(1) + \Delta H_s(2) + \Delta H_s(3) + \Delta H_s(4) + \Delta H_s(5) + \Delta H_s(6) \qquad (4)$$

As stated earlier herein, across any single interval, the surface-measured tool characteristic may be approximated by a straight line segment. The algebraic slope of each such segment may be designated as:

$$(dH/df)\,(I) \qquad (5)$$

where dH represents the change in the volumetric fraction of water, df represents the change in dielectric response sensor frequency and I represents the number of the interval. Thus, the change in the volumetric fraction of water across any single interval ($\Delta H_s(I)$) may be determined by the relation:

$$\Delta H_s(I) = \frac{dH}{df}(I) \times \Delta f(I) \qquad (6)$$

where $\Delta f(I)$ represents the change in frequency across the interval. In the illustrated example, this is the change in frequency across the full interval in intervals two through five, or, in the case of intervals 1 and 6 in which points $H_s(100)$ and $H_s(L)$ are located, the change in frequency within that portion of each of the intervals lying between the two extremes, $H_s(100)$ and $H_s(L)$.

The degree to which the change in the apparent volumetric fraction of water in any single interval ($\Delta H_s(I)$) contributes to the apparent total change in the volumetric fraction of water ($\Delta H_s$), termed the participation factor ($P(I)$) of such interval, is then determined:

$$P(I) = \frac{\Delta H_s(I)}{\Delta H_s} \qquad (7)$$

It will be appreciated that the sum of all $P(I)$ is unity. These participation factors $P(I)$ from the surface characteristics are now correlated with the volumetric fractions of water determined from the density measurements.

Figure 9:
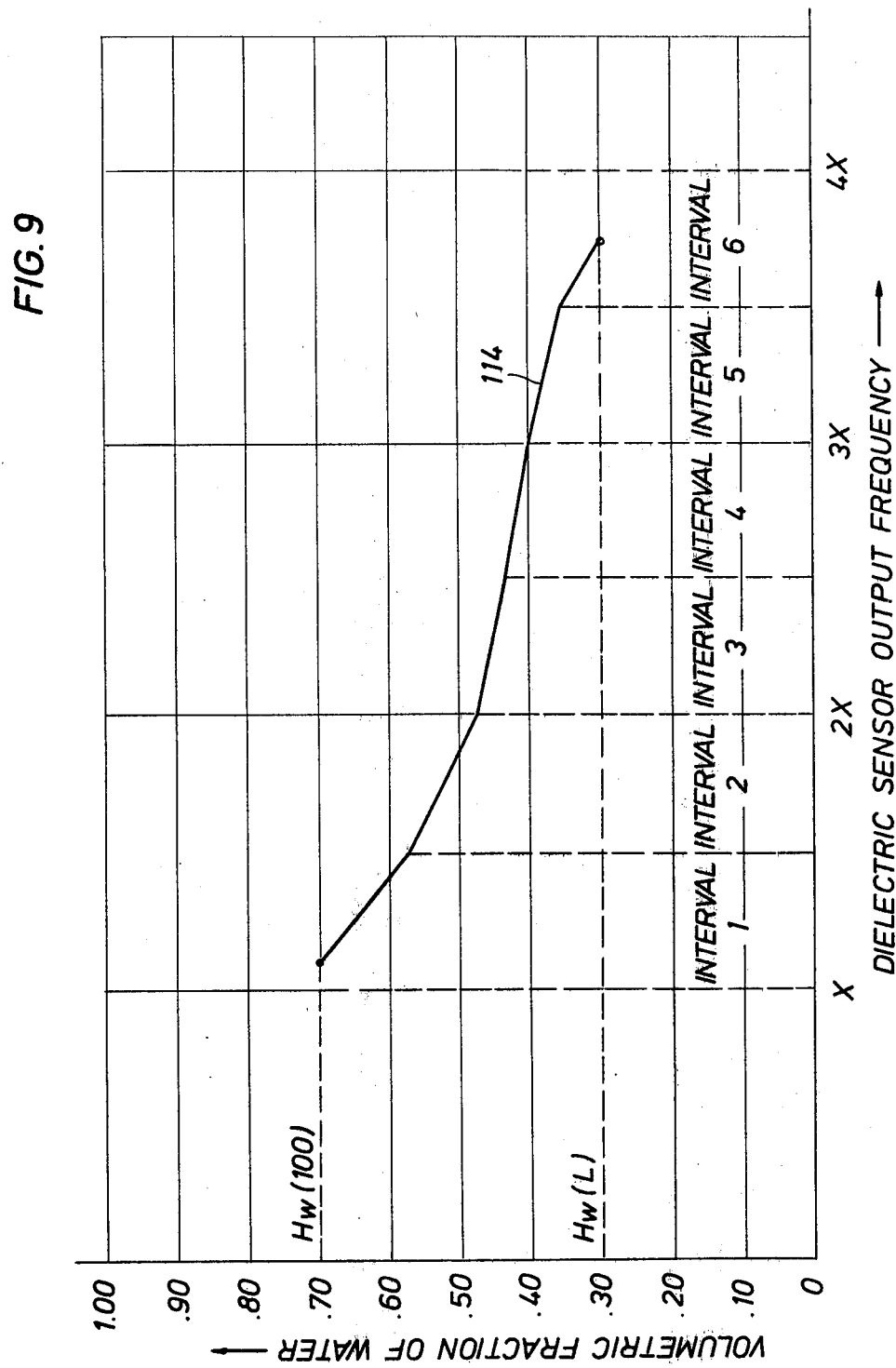
FIG. 9 illustrates graphically the response curve of FIG. 8, adjusted in accordance with the present invention.

The total change in the volumetric fraction of water according to the density measurement ($\Delta H_w$) is determined by the relation:

$$\Delta H_w = H_w(100) - H_w(L) \qquad (8)$$

where $H_w(100)$ represents the maximum volumetric fraction of water determined from the density measurement and $H_w(L)$ represents the minimum volumetric fraction of water determined from the density measurement. Therefore, utilizing the participation factor ($P(I)$) of each interval to relate the apparent change in the volumetric fraction of water ($\Delta H_s$) to the established change in the volumetric fraction of water ($\Delta H_w$), the shape of the surface-derived response curve 108 may be preserved by determining the corrected change in the volumetric fraction of water across each interval in accordance with the relationship:

$$\Delta H_w(I) = \Delta H_w \times P(I) \qquad (9)$$

for each significant interval (in the example, intervals 1-6), and linearly approximating the functional relationships across each interval by sequentially correlating each $\Delta H_w(I)$ to each $f(I)$, by either adding the appropriate $\Delta H_w(I)$ value to $H_w(L)$ or subtracting the appropriate $\Delta H_w(I)$ value from $H_w(100)$ across each interval. Thus response curve 108 of the dielectric response sensor, indicating the functional relationship between the tool output frequency and the volumetric fraction of water, is approximated and translated in relation to downhole well conditions in view of generally reliable determinations of the volumetric composition of the fluid flow regime, as illustrated in curve 114 in FIG. 9. Subsequent dielectric response sensor measurements within well 113 may now be corrected for quantitative errors induced by downhole conditions within well 113. It will be appreciated that if a reference is established for an embodiment of a dielectric response sensor which evidences a linear functional relation between the measured dielectric response of a mixture of two fluids to the volumetric fraction represented by at least one of the fluid phases, at least over the range of dielectric response values encountered within the well (between those points represented as $H_s(100)$ and $H_s(L)$ in the preceeding example), then a graphic representation of such reference will have a constant slope over such range and may be regarded as a single interval which may then be adjusted in reference to the density-derived volumetric fractions in the manner described above.

Utilizing the functional relationships so established, and expressed in the corrected response curve (114 in FIG. 9), a scale may be established for improved interpretation and presentation of subsequent dielectric response sensor readings taken within the well (113 in FIG. 7). In the preferred practice of the present invention this scale will be applied to a conventional graphic well log presentation. The scale may be applied in a variety of ways. In the preferred embodiment of the present invention, uniform volumetric fraction of water values are pre-assigned to each chart division of the log, preferably in even multiples, such as twenty chart divisions, each representing a 5% increment in the volumetric fraction of water between 0 and 100%. Subsequent dielectric response sensor measurements are then correlated to the functional relationships expressed by the corrected response curve (114 in FIG. 9), and are then plotted accordingly on the pre-established scale.

Once the corrected response curve (114 in FIG. 9), and the scale or scaling system are established, instrument 1 is moved to another depth location within the zone of interest in the well, represented at 126 or 128 in FIG. 7. The flow collector is opened and flow rate and dielectric response measurements are taken over a predetermined time period in a manner similar to that described earlier herein. In the preferred embodiment, the simple average of each of the timed measurements is taken in the manner described earlier herein and these averages are plotted on the well log, the average dielectric response measurement being correlated to the functional relationships expressed on the corrected response curve (114 in FIG. 9) and plotted accordingly on the pre-established scale. Similarly, the average total flow rate measurement may be plotted on an appropriate scale established in a conventional manner. Alternatively, the timed dielectric response sensor signal may be correlated in its entirety to volumetric fractions of water and thereafter plotted in its entirety in relation to the established scale and a simple average taken of the plotted volumetric fractions of water thus represented. Similarly, the flow rate measurement signal may also be plotted on the well log in its entirety and an average measurement value taken of such plotted signal. It will be appreciated that the present invention contemplates either of the above correlations being done either in real time or during later processing either at or remote from the well site. Obviously, the volumetric fraction of the oil phase of the fluid flow regime may also be determined at these locations in accordance with the relationship expressed in equation 2 and may similarly be graphically plotted on the well log.

Because all of the three described measurements of characteristics of the fluid flow regime are conducted as the fluid flow regime has been collected and accelerated through the relatively small chamber within instrument 1, the effects of slippage between the two phases may be considered negligible. As a result, there may be considered to exist a direct functional relationship between the determined fluid phase volumetric fractions and the flow rates of the individual fluid phases. Using the total measured flow rate expressed in barrels per day ($BPD_T$) at any depth location 110, 112, 126 or 128 and the individual fluid phase volumetric fraction determined as described earlier herein at that depth location 110, 112, 126 or 128 ($H_w$) and ($H_o$) for water and oil, respectively), the flow rate of each individual phase, ($BPD_w$) and ($BPD_o$) for water and oil, respectively, may be expressed in accordance with the relations:

$$BPD_w = H_w \times BPD_T \quad (10)$$

and $$BPD_o = H_o \times BPD_T \quad (11)$$

where all terms represent data at a single specific depth location 110, 112, 126, or 128 within well 113. The individual phase flow rates so determined may be similarly plotted on the graphic well log on appropriate scales, either in conjunction with or in place of the determined volumetric fractions of the fluid phases.

It is to be appreciated that the three fluid property sensors may be located in two or more logging instruments rather than contained within a single instrument. Thus, two or more logging operations may be required to obtain the necessary data. Such data may, however, be correlated in the manner described herein. Such multiple logging operations are not the preferred practice of the present invention, however, because of an increased probability of error due to alterations in detected well flow conditions between data measurements. It will be noted that where the data is to be collected in multiple logging operations, it may be preferable to include a suitable form of data storage (105 in FIG. 1) in the surface electronics (indicated generally at 14 in FIG. 1) as described earlier herein, to facilitate processing of the data.

Figure 10A:
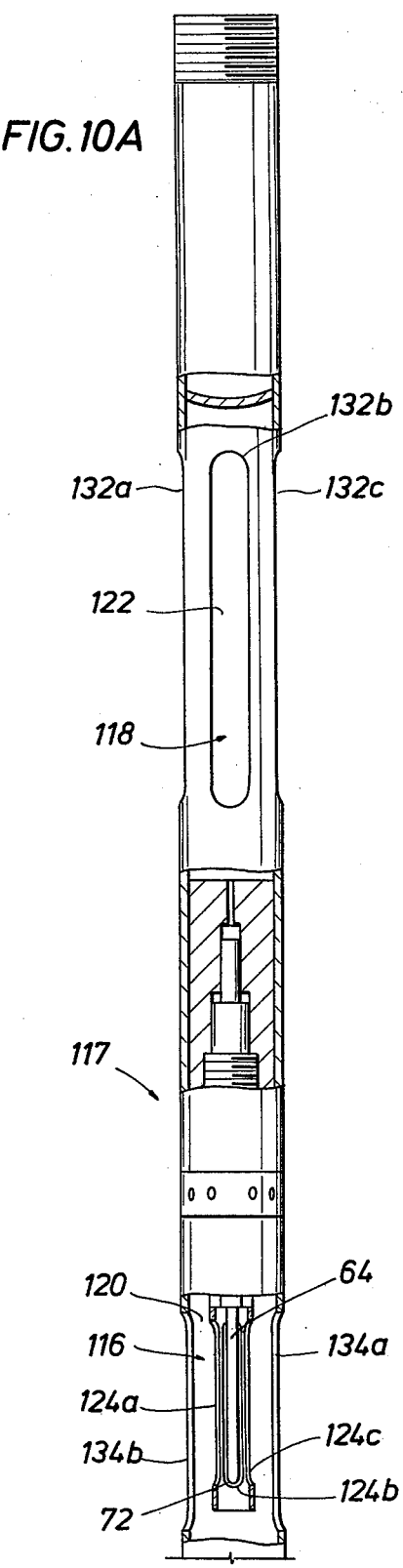
FIGS. 10 A and B illustrate an alternative embodiment of a logging instrument in accordance with the present invention, illustrated partially in cutaway view.
Figure 10B:
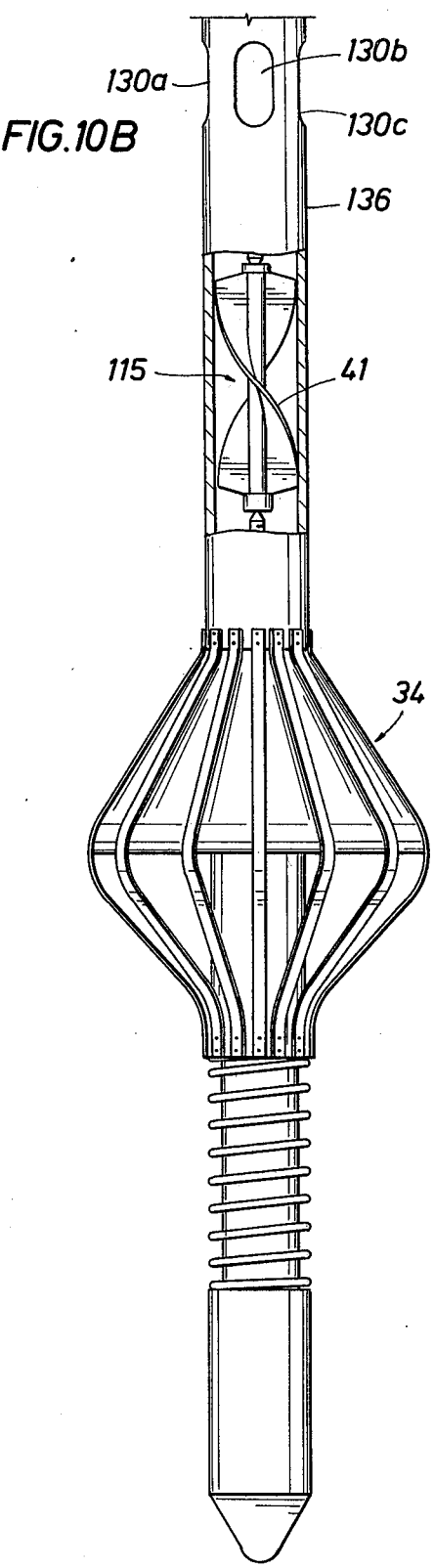

In an alternative embodiment of the invention, the density and dielectric response of the well fluid may be measured after the fluid has returned to the well from within the instrument where the fluid flow rate is determined. A single instrument suitable for making this type of measurement is shown in FIG. 10, illustrated partially in cut-away views. Elements equivalent to those in the previous embodiment have been numbered similarly. Each fluid property sensor 115, 116 and 118 functions essentially in the manner herein described with respect to the previous embodiment with the exceptions that dielectric response sensor 116 and density sensor 118 are now located within their own chambers 120 and 122 which are in free-flowing fluid communication with the well.

In the operation of this embodiment of the invention, instrument 117 is lowered to the depth location at which a measurement is desired and collector 34 is opened in the manner described earlier herein. The well fluid enters and is accelerated and mixed into a generally uniform mixture by collector 34, and contacts and rotates rotor 41 to generate a first electrical signal as described previously. The generally uniform mixture then exits body member 136 through apertures 130a, 130b and 130c and returns to the well. As the generally uniform mixture passes instrument 117, a portion of the mixture will enter dielectric response sensor chamber 120 through apertures 134a and 134b. The mixture will further enter annulus 72 between electrodes 64 and 135 of dielectric response sensor 116 to generate a second electrical signal as described earlier herein. It will be noted that hollow cylindrical electrode 135 of dielectric response sensor 116 contains larger apertures 124a, 124b and 124c adapted for improved cross-flow of fluids between electrodes 64 and 135. As the mixture continues to pass instrument 117, a portion of the mixture will traverse density chamber 122 through apertures 132a, 132b and 132c, wherein a third electrical signal will be generated by density sensor 118 in a manner similar to that described for the previous embodiment. It will be appreciated that the preferred embodiment of the invention contemplates mixing the fluid flow regime into a generally uniform mixture and determining the density and dielectric response characteristics of such mixture. Where the density and dielectric response determinations are made after the mixture has returned to the well, due to the decreased velocity and and absence of mixing effects, as the mixture passes instrument 117 the mixture may begin to separate into its constituent phases. Therefore, it is desirable to make the density and dielectric response determinations in as close proximity to the point of discharge from within instrument 117 as possible to minimize the separation occurring before the determinations are made. As with the embodiment of the invention described previously, the sensors may again be located within a plurality of logging instruments rather than within a single instrument as is illustrated in FIG. 10.

In the practice of this alternative embodiment of the invention, the measurements are taken, the response curve corrected, and values of $H_w$ obtained in reference to such response curve for each depth location in the manner described for the previous embodiment, however, additional considerations are presented by the measurement of the fluid properties after the mixture has returned to the well bore.

When the fluid density and dielectric response measurements are made after the fluid has returned to the well bore, the accelerated velocity of the fluid which was achieved within the limited confines of instrument 117 has been lost and slippage between the two phases becomes a significant parameter which must be taken into consideration. Once the volumetric fraction of water ($H_w$) at each depth location has been determined in the manner described for the previous embodiment, this phase slippage may be accounted for by adjusting the volumetric fraction of water ($H_w$) in accordance with the relation:

$$H_w(C) = H_w - \frac{AV_s 256.20 H_w}{BPD_T}(1 - H_w) \quad (12)$$

where $H_w(C)$ represents the corrected volumetric fraction of water, A represents the area of the annulus between the logging instrument and the inner perimeter of the well bore is square feet, 256.20 is a conversion factor for converting cubic feet to barrels per day, and $V_s$ represents the slip velocity between the phases expressed in feet/min. Because there is no direct measurement of $V_s$, the term must be established in reference to empirical measurements made before the described correction is attempted. Determinations of the slippage between phases should occur in reference at least to flow rates, phase densities, and the angle of deviation of the pipe containing the fluid flow regime. From tests of phase slippage under such conditions, an appropriate value for $V_s$ may be selected for use in the described correction. The corrected oil holdup $H_o(C)$ may be expressed by the relation:

$$H_w(C) = (1 - H_w) + \frac{AV_s 256.20 H_w}{BPD_T}(1 - H_w) \quad (13)$$

In a manner similar to that described for the first embodiment of the invention, the corrected fluid phase volumetric fractions so determined may be related to the flow rates of the water and oil phases by multiplying the corrected volumetric fractions of the two phases, $H_w(C)$ and $H_o(C)$, by the total fluid flow rate as determined at the same location in the well:

$$BPD_w = H_w(C) \times BPD_T \quad (14)$$

and $$BPD_o = H_o(C) \times BPD_T \quad (15)$$

As with the previous embodiment, the present invention contemplates that any of the described measured values, corrected or uncorrected may be plotted on appropriate scales upon the well log.

Many modifications and variations besides those specifically mentioned may be made in the techniques and structures described herein and depicted in the accompanying drawings without departing substantially from the concept of the present invention. Accordingly, it should be clearly understood that the forms of the invention described and illustrated are exemplary only and are not intended as limitations on the scope of the present invention.

The embodiments of the invention in which an exclusive property or privilege is claimed are defined as follows:

1. A method for determining characteristics of a multi-phase fluid flow regime, comprising the steps of:
    (a) measuring the density of said fluid flow regime;
    (b) measuring dielectric response characteristics of said fluid flow regime; and
    (c) establishing a functional relationship between said dielectric response characteristics measurement of said fluid flow regime and the volumetric fraction of at least one phase of said fluid flow regime, said functional relationship established in reference to said measured density of said fluid flow regime.

2. The method for determining characteristics of a multi-phase fluid flow regime of claim 1, wherein step (c) comprises the steps of:
    (d) establishing as a reference, the functional relationships between measured dielectric response characteristics of a fluid consisting of multiple fluid phases and the volumetric fractions of said fluid represented by at least one of said phases thereof;
    (e) determining the volumetric fraction of said fluid flow regime represented by at least one phase of said fluid flow regime in response to said density measurement of step (a); and
    (f) adjusting said reference of step (d) in response to said volumetric fraction determination of step (e).

3. A method for determining characteristics of a multi-phase fluid flow regime within a well, comprising the steps of:
    (a) determining the density of said fluid flow regime at a first location within said well;
    (b) determining dielectric response characteristics of said fluid flow regime at said first location within said well;
    (c) determining the density of said fluid flow regime at a second location within said well;
    (d) determining dielectric response characteristics of said fluid flow regime at said second location within said well; and
    (e) establishing functional relationships between the dielectric response characteristics of said fluid flow regime and the volumetric fraction of at least one phase within said fluid flow regime in reference to said density determinations of steps (a) and (c) and said dielectric response characteristics determinations of steps (b) and (d).

4. The method for determining characteristics of a multi-phase fluid flow regime of claim 3, further comprising the steps of:
    (f) blending said fluid flow regime into a generally uniform mixture at said first location within said well; and
    (g) blending said fluid flow regime into a generally uniform mixture at said second location within said well.

5. The method for determining characteristics of a multi-phase fluid flow regime of claim 4, wherein said density determination of step (a) and said dielectric response characteristics determination of step (b) are determined of the generally uniform mixture of said fluid flow regime of step (f), and wherein said density determination of step (c) and said dielectric response characteristics determination of step (d) are determined of the generally uniform mixture of said fluid flow regime of step (g).

6. The method for determining characteristics of a multi-phase fluid flow regime of claim 3, further comprising the steps of:

(h) determining the volumetric fraction of at least one phase of said fluid flow regime at said first location within said well in response to said density determination of step (a); and (i) determining the volumetric fraction of at least said one phase of said fluid flow regime at said second location within said well in response to said density determination of step (c).

7. The method for determining characteristics of a multi-phase fluid flow regime of claim 6, wherein step (e) comprises:

(j) establishing as a reference, the functional relationships between the dielectric response characteristics of a fluid having at least two fluid phase components and the volumetric fraction of said fluid represented by at least one of said fluid phase components; and (k) adjusting said reference such that interpreting said dielectric response characteristics determation of step (b) in response to said reference of step (j) indicates a volumetric fraction of said one phase of said fluid flow regime generally equivalent to that volumetric fraction of said one phase determined in step (h), and, such that interpreting said dielectric response characteristics determination of step (d) in response to said reference of step (j) indicates a volumetric fraction of said one phase of said fluid flow regime generally equivalent to the volumetric fraction of said one phase determined in step (i).

8. The method of determining characteristics of a multi-phase fluid flow regime of claim 6, further comprising the steps of:

(l) determining the flow rate of said fluid flow regime at said first location within said well;

(m) determining the flow rate of said fluid flow regime at said second location within said well;

(n) determining the flow rate of at least one phase of said fluid flow regime at said first location within said well in response to said flow rate determination of step (l) and said volumetric fraction determination of step (h); and (o) determining the flow rate of at least one phase of said fluid flow regime at said second location within said well in response to said flow rate determination of step (m) and said volumetric fraction determination of step (i).

9. The method for determining characteristics of a multi-phase fluid flow regime of claim 6, further comprising the steps of:

(p) determining the dielectric response of said fluid flow regime at a third location within said well;

(q) determining the volumetric fraction of at least said one phase of said fluid flow regime at said third location within said well in accordance with said dielectric response determination of step (p) and said functional relationships established in step (e).

10. The method for determining characteristics of a multi-phase fluid flow regime of claim 9, further comprising the steps of:

(r) measuring the flow rate of said fluid flow regime at said third location within said well;

(s) determining the flow rate of at least said one phase of said fluid flow regime at said third location within said well in response to said flow rate determination of step (r) and said volumetric fraction determination of step (q).

11. A method for determining characteristics of a fluid flow regime within a well, said fluid flow regime having at least two phases, comprising:

(a) establishing as a reference, the functional relations between the measured dielectric response characteristics of a sample mixture of multiple fluid phases and the volumetric fraction of at least one of said multiple fluid phases in said sample mixture, said multiple fluid phases within said sample mixture being essentially the same as those fluid phases within said fluid flow regime;

(b) blending at least a portion of said fluid flow regime into a first mixture of generally uniform composition at a first location within said well;

(c) determining the density of said first mixture of generally uniform composition;

(d) determining the dielectric response of said first mixture of generally uniform composition;

(e) blending at least a portion of said fluid flow regime into a second mixture of generally uniform composition at a second location within said well;

(f) determining the density of said second mixture of generally uniform composition;

(g) determining the dielectric response of said second mixture of generally uniform composition;

(h) determining the volumetric fraction of at least a first phase of said fluid flow regime at said first location within said well in response to said density determination of step (c);

(i) determining the volumetric fraction of said first phase of said fluid flow regime at said first location within said well in accordance with said dielectric response determination of step (d) and said reference established in step (a);

(j) determining the volumetric fraction of said first phase of said fluid flow regime at said second location in said well in response to said density determination of step (f);

(k) determining the volumetric fraction of said first phase of said fluid flow regime at said second location within said well in accordance with said dielectric response determination of step (g) and said reference established in step (a); and (l) adjusting said reference established in step (a) in response to said determinations of steps (h) and (j).

12. The method for determining characteristics of a fluid flow regime of claim 11, wherein step (l) comprises:

(m) determining the change in the volumetric fractions of said first phase between said first and second locations as reflected by said volumetric fraction determinations of steps (h) and (j);

(n) determining the indicated change in the volumetric fraction of said first phase of said fluid flow regime between said first and second locations as reflected by said volumetric fraction determinations of steps (i) and (k);

(o) dividing said reference established in step (a) into a plurality of intervals at least over the portion of said reference functionally corresponding to said volumetric fraction determinations of steps (i) and (k);

(p) establishing the change in said volumetric fractions of said reference established in step (a) over each of said intervals of step (o);

(q) establishing the proportional amount of said indicated change in volumetric fraction of said first phase of step (n) which is represented by said change in volumetric fractions over each interval of step (p); and (r) adjusting said functional relationships of said reference of step (a) in response to said proportional amounts of change in volumetric fractions of step (q) and said determined change in volumetric fractions of step (m).

13. The method for determining characteristics of a fluid flow regime of claim 12, wherein step (r) further comprises linearly approximating said functional relationships over the span of each of said intervals of step (o).

14. The method for determining characteristics of a fluid flow regime of claim 11, wherein said volumetric fraction determination of step (h) comprises the steps of:

(s) measuring the density of each of said fluid phases within said fluid flow regime; and (t) determining said volumetric fraction in reference to said determined density of said mixture of step (c) and said measured densities of each of said fluid phases of step (s).

15. The method for determining characteristics of a fluid flow regime of claim 11, wherein said volumetric fraction detemination of step (j) comprises the steps of:

(u) measuring the density of each of said fluid phases within said fluid flow regime; and (v) determining said volumetric fraction in reference to said determined density of said mixture of step (f) and said measured densities of each of said fluid phases of step (u).

16. The method for determining characteristics of a fluid flow regime of claim 11, further comprising the step of establishing a response curve exhibiting the functional relationships between the determined dielectric response of a mixture of said fluid flow regime within said well and the volumetric fraction of at least one of said fluid phases within said fluid flow regime.

17. The method for determining characteristics of a fluid flow regime of claim 11, further comprising the steps of:

(w) measuring the flow rate of said first mixture of generally uniform composition of step (b); and (x) determining the flow rate of at least said first phase of said fluid flow regime at said first location within said well in reference to said volumetric fraction determination of step (h) and said flow rate measurement of step (w).

18. The method for determining characteristics of a fluid flow regime of claim 11, further comprising the steps of:

(y) measuring the flow rate of said second mixture of generally uniform composition of step (e); and (z) determining the flow rate of at least said first phase of said fluid flow regime at said second location within said well in reference to said volumetric fraction determination of step (j) and said flow rate determination of step (y).

19. The method for determining characteristics of a fluid flow regime of claim 11, further comprising the steps of:

(aa) blending at least a portion of said fluid flow regime into a third mixture of generally uniform composition at a third location within said well;

(bb) determining the dielectric response of said third mixture of generally uniform composition; and (cc) determining the volumetric fraction of said first phase of said fluid flow regime at said third location within said well in response to said dielectric response determination of said third mixture of step (bb) and to said adjusted reference of step (l).

20. The method for determining characteristics of a fluid flow regime of claim 19, further comprising the steps of:

(dd) measuring the flow rate of said third mixture of generally uniform composition of step (aa); and (ee) determining the flow rate of at least said first phase of said fluid flow regime at said third location within said well in reference to said volumetric fraction determination of step (cc) and said flow rate determination of step (dd).

21. The method for determining characteristics of a fluid flow regime of claim 19, further comprising the step of:

(ff) adjusting said volumetric fraction determination of step (cc) to compensate for slippage between said phases of said fluid flow regime.

22. The method for determining characteristics of a fluid flow regime of claim 21, further comprising the steps of:

(gg) measuring the flow rate of said third mixture of generally uniform composition of step (aa); and (hh) determining the flow rate of at least said first phase of said fluid flow regime at said third location within said well in reference to said adjusted volumetric fraction determination of step (ff) and said measured flow rate of step (gg).

23. The method for determining characteristics of a fluid flow regime of claim 11, further comprising the step of:

(ii) adjusting said volumetric fraction determination of step (h) to compensate for slippage between said phases of said fluid flow regime.

24. The method for determining characteristics of a fluid flow regime of claim 23, further comprising the steps of:

(jj) measuring the flow rate of said first mixture of generally uniform composition of step (b); and (kk) determining the flow rate of at least said first phase of said fluid flow regime at said first location within said well in reference to said adjusted volumetric fraction determination of step (ii) and said measured flow rate of step (jj).

25. The method for determining characteristics of a fluid flow regime of claim 11, further comprising the steps of:

(ll) adjusting said volumetric fraction determinations of step (j) to compensate for slippage between said phases of said fluid flow regime.

26. The method for determining characteristics of a fluid flow regime of claim 25, further comprising the steps of:

(mm) measuring the flow rate of said second mixture of generally uniform composition of step (e); and (nn) determining the flow rate of at least said first phase of said fluid flow regime at said second location within said well in reference to said adjusted volumetric fraction determination of step (ll) and said measured flow rate of step (mm).

* * * * *